United States Patent
Kensuke et al.

(10) Patent No.: US 7,002,096 B2
(45) Date of Patent: Feb. 21, 2006

(54) SURFACE MODIFICATION PROCESS ON METAL DENTURES, PRODUCTS PRODUCED THEREBY, AND THE INCORPORATED SYSTEM THEREOF

(75) Inventors: Uemura Kensuke, Kamakura (JP); Uehara Seigo, Fujisawa (JP); Raharjo Purwadi, Nishikanbara-Gun (JP); Proskurovsky Dmitri Il'ich, Tomsk (RU); Ozur Grigorii Evgen'evich, Tomsk (RU); Rotshtein Vladimir Petrovich, Tomsk (RU)

(73) Assignee: Itac Limited, Tokyo (JP)

( * ) Notice: Subject to any disclaimer, the term of this patent is extended or adjusted under 35 U.S.C. 154(b) by 13 days.

(21) Appl. No.: 10/850,409

(22) Filed: May 19, 2004

(65) Prior Publication Data

US 2004/0214139 A1 Oct. 28, 2004

Related U.S. Application Data

(62) Division of application No. 09/893,138, filed on Jun. 28, 2001, now Pat. No. 6,863,531.

(51) Int. Cl.
*A61C 13/00* (2006.01)
*A61C 13/20* (2006.01)
*A61C 17/00* (2006.01)
*B23P 9/00* (2006.01)

(52) U.S. Cl. .................................. 219/121.17
(58) Field of Classification Search ............ 219/121.12, 219/121.16, 121.17, 121.19, 121.2, 121.35; 433/200.1
See application file for complete search history.

(56) References Cited

U.S. PATENT DOCUMENTS 4,229,232 A * 10/1980 Kirkpatrick ................. 148/512
5,013,243 A * 5/1991 Tanaka et al. .............. 433/189

FOREIGN PATENT DOCUMENTS

JP          02295557 A  * 12/1990

* cited by examiner

*Primary Examiner*—Samuel M. Heinrich
(74) *Attorney, Agent, or Firm*—Jordan and Hamburg LLP

(57) ABSTRACT

Metal and/or partial metal dentures having a surface modified by a pulsed electron beam system. The system includes an explosive emission cathode, an accelerating gap formed by the cathode and plasma anode, and an electron collector where the metal and/or partial metal dentures are fixed, and placed into a magnetic field. The surface of the modified metal and/or partial metal denture has high reflectance like a mirror polished surface and high corrosion resistance.

18 Claims, 7 Drawing Sheets

US 7,002,096 B2

SURFACE MODIFICATION PROCESS ON METAL DENTURES, PRODUCTS PRODUCED THEREBY, AND THE INCORPORATED SYSTEM THEREOF

CROSS-REFERENCE TO RELATED APPLICATION

This application is a divisional of U.S. patent application Ser. No. 09/893,138 filed Jun. 28, 2001, now U.S. Pat. No. 6,863,531 the specification of which is incorporated by reference herein.

FIELD OF THE INVENTION

The present invention relates to full and partial metal dentures having a polished surface.

BACKGROUND OF THE INVENTION

The need for dentures is too valuable to detail here. It is also human history to seek better dentures to maintain a healthy lifestyle by increasing the pleasure of the table, i.e., the pleasure obtained from eating.

There are some materials from which dentures are made such as plastics, ceramics, metals and others. Metal or partial metal dentures are dentures made with metal materials, which is now thought to be the best materials.

Metal materials are roughly classified into three categories, namely, Titanium System Alloys, Cobalt System Alloys and Precious System Alloys.

As a recent trend, the Titanium System Alloys are primarily used, while on the other hand, Precious System Alloys are used quite infrequently due to their deformation phenomena or heavier weight.

The features of metal and/or partial metal dentures are that they provide a good fit in the mouth, an immediate reaction to hot foods in the mouth due to their high thermal conductivity and they are lightweight, at least in the case of Titanium System Alloys.

On the other hand, fabricating metal and/or partial metal dentures requires the dental technicians to have a lot of experience and skills. Therefore, it takes a relatively long time to fabricate metal and/or partial metal dentures, and they usually have high costs.

To fabricate the metal and/or partial metal dentures, there are several steps, first melting the alloys, then casting the melted alloys in the mold and finally finishing the surface with small, hand-held diamond abrasive tools.

After de-molding, the cast metal and/or partial metal dentures are typically finished by a well-experienced dental technician with handy tools, therefore the technician is able to finish one metal and/or partial metal denture in two or three hours or in half day at the longest. Moreover, the surface finishing in the process is designed to remove the cast skin layer from the metal and/or partial metal dentures and fit the shape of the wearer's mouth, then the surfaces are corroded by the acid in the wearer's stomach to change the color from metallic to black

SUMMARY OF THE INVENTION

In dentures in accordance with the invention, electron beams in pulsed repetition are bombarded onto the total or entire surface of the substrate of the metal and/or partial metal dentures which provide the form of teeth and are adapted for insertion into a wearer's mouth. The surface of the metal and/or partial metal dentures as it is after the cast is melted is turned into amorphous surface by the pulsed repetition of the electron beams. This eliminates the time and cost of the processing of the cast metal and/or partial metal dentures with diamond tools by a well-experienced dental technician. Due to amorphous metal surface, the electron beam treated surface shows 2 to 5 times stronger resistance against accelerated hydrochloride acid solution.

The invention contributes to a reduction in the time to provide the metal and/or partial metal dentures to several minutes from hours of fabrication as in the prior art; moreover, its acid corrosion resistance is dramatically increased to enable the dentures to last for long years of use.

DETAILED DESCRIPTION OF THE INVENTION

Figure 1:
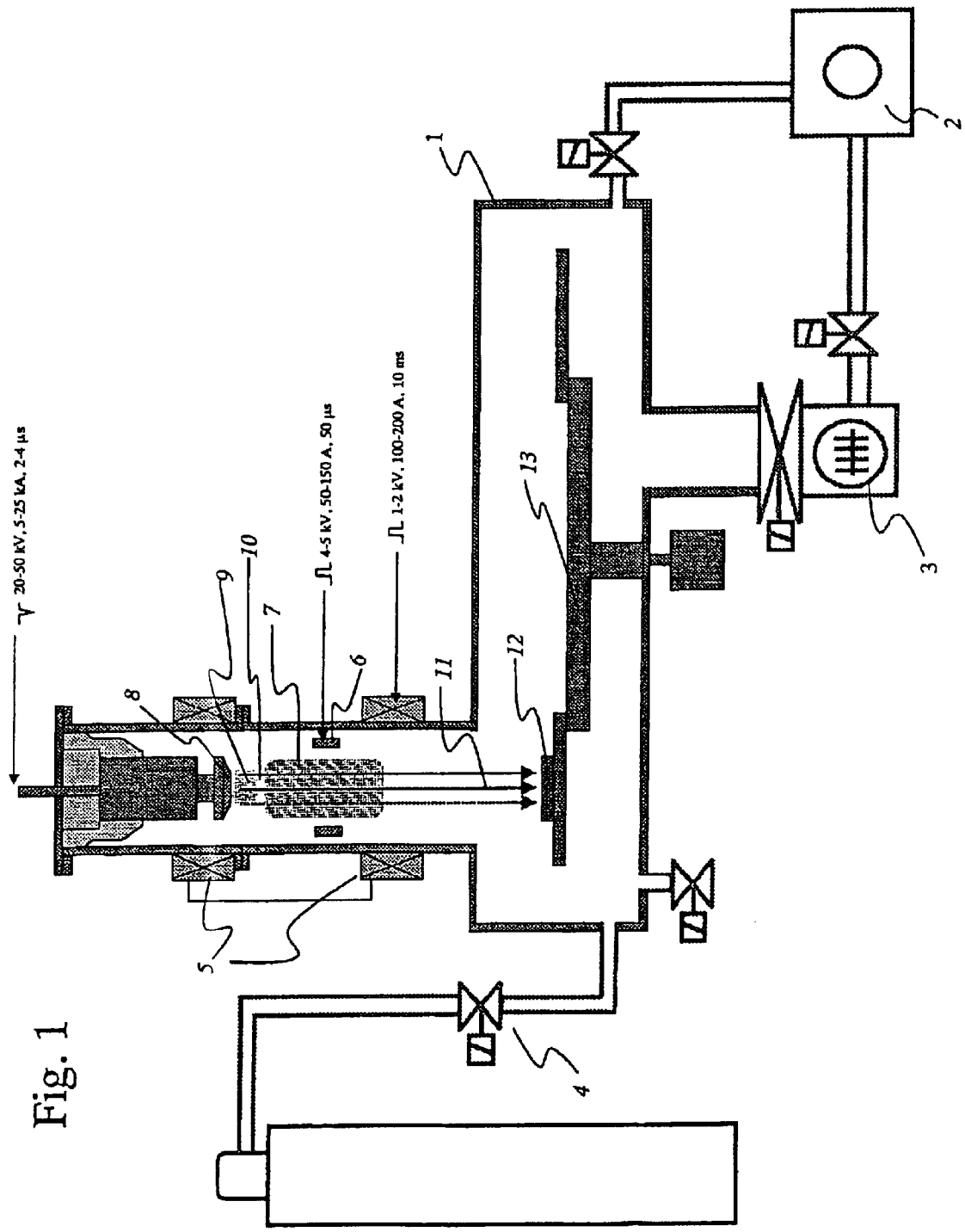
FIG. 1 shows the schematic general assembly of a pulsed electron beam system, which was used to modify the surface of the metal and/or partial metal dentures in accordance with the invention.

The schematic assembly of Pulsed Electron Beam System is shown in the FIG. 1. The vacuum chamber is made of stainless steel. The original vacuum degree is about $10^{-2}$ Pa and Argon gas is partially filled into the chamber. The cumulated energy is discharged from the cathode to the collector through a double layer between the cathode plasma and the anode plasma column. For formation of the plasma column, a high current reflected (Penning) discharge in Ar working gas is applied.

The pulsed electron beam system has an anode with the shape of a ring or topological similar to it (for example rectangular, polygonal ring structure etc.), which is installed in a position where the axis of the ring is parallel to the beam transportation path. This position provides a benefit of preventing a decrease of beam current caused by collision of electrons on the anode surface.

Figure 2:
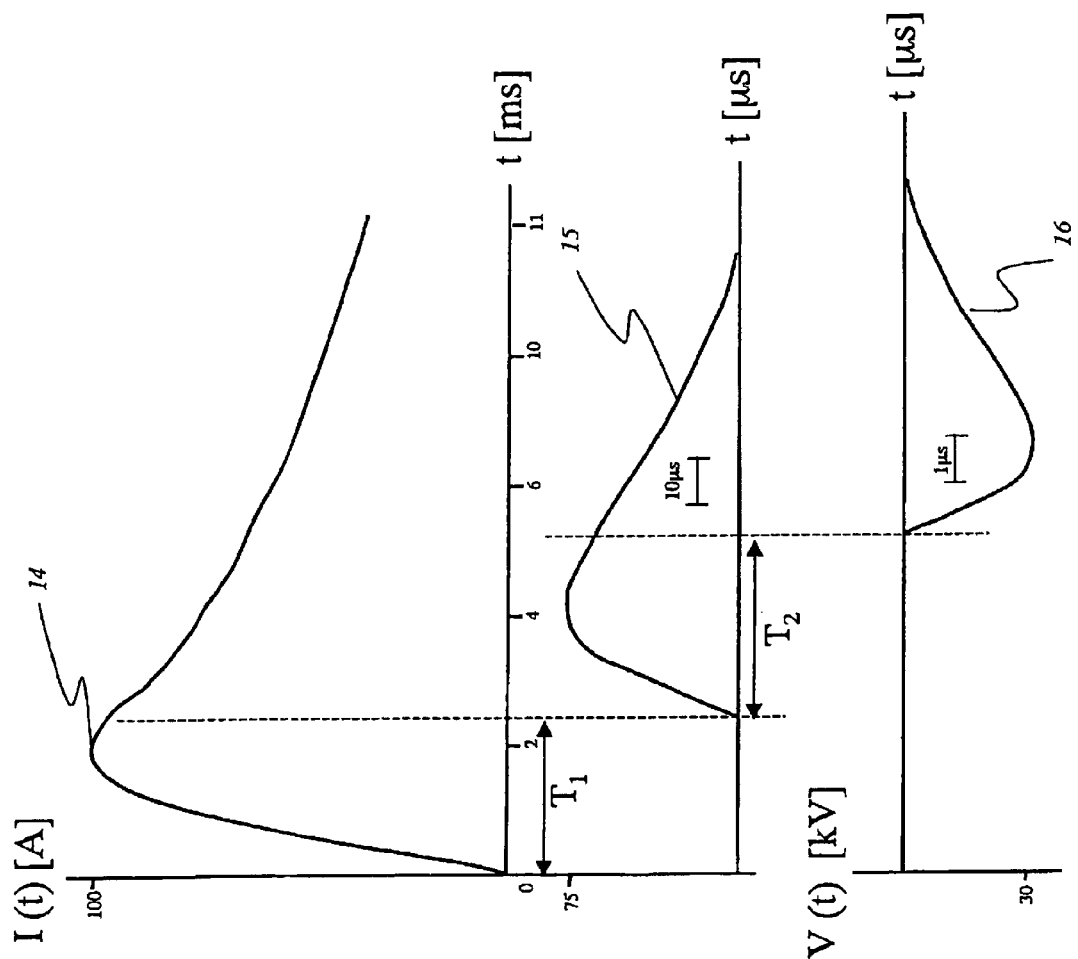
FIG. 2 indicates a typical operating condition as accelerated voltage and beam current.
Figure 3:
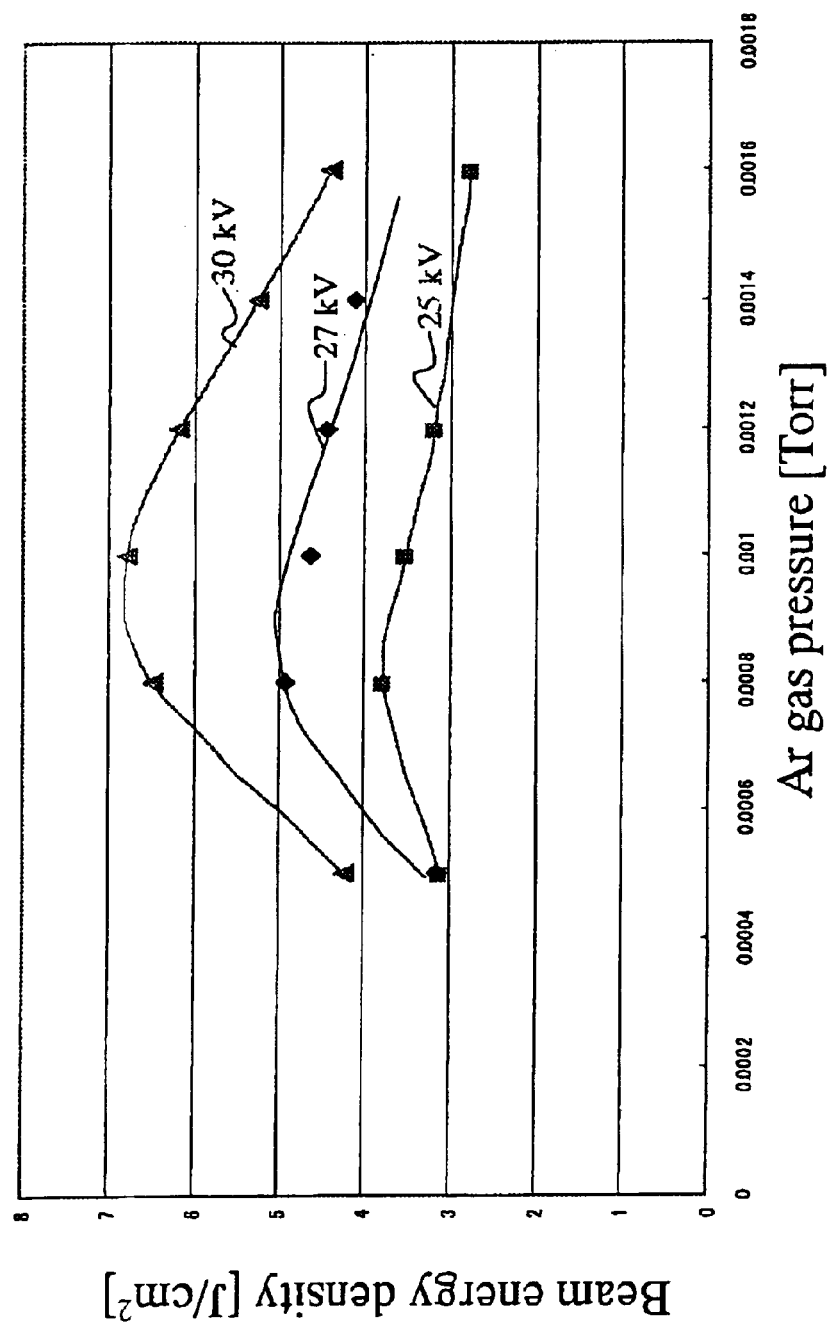
FIG. 3 shows the operation data in the pulsed electron beam system in which in the chamber, there exists partial Argon gas in vacuum chamber and the beam irradiated onto the metal and/or partial metal dentures

Detailed processes of electron beam treatment are described as follows. After setting the sample on the sample holder and closing the chamber lid, the chamber 1 is evacuated from atmospheric pressure until the initial background pressure is obtained by using a scroll pump 2 for roughing vacuum and turbo molecular pump 3 for high vacuum evacuation. Then, Ar gas is filled in the chamber 1 and its pressure is adjusted up to a certain pressure between $0.5-3\times10^{-1}$ Pa by using a flow control valve 4. After reaching the setting pressure, a pulse guide magnetic field with strength up to 4.4 kOe is created by two external solenoids 5. In FIG. 2, a typical current pulse of solenoid 14 is shown. During the generation of the magnetic field, a positive pulse high voltage (about 5 kV) with anode pulse current 15 is applied to a ring-shaped anode 6 to obtain an intensive anode-plasma 7 by a reflected Penning discharge method. As another method, anode plasma might be produced simply by arc discharge, but the method would wear out the electrode, which may lead to chamber contamination. Moreover, comparing the consuming current, the arc discharge needs higher current than the present method.

After obtaining high current stage of anode plasma current (generally 20–50 μs after applying voltage on the anode), a negative accelerating voltage pulse 16 with an amplitude below 50 kV and rise time of 5–10 ns is applied to the electron gun cathode 8. An intensive electric field between the cathode and the near-cathode layer of the ionic space charge, can reach to considerable values up to 500 kV/cm and is enough to initiate an explosive electron emission for formation of a dense cathode-plasma 9. The accelerating voltage applied on the anode and cathode is concentrated in a double layer 10 created between the cathode and anode plasmas, where the high current electron beam 11 is formed. The electron beam current density in the double layer is related to the anode plasma ion current density by Langmuir law.

The electron beam accelerated in the double layer 10 is transported through the anode plasma to the beam collector, on which the samples is placed. Owing to the ionic space charge by the anode plasma ions in the present system, the high current electron beam can be more stable compared to beams in a vacuum. As usually occurred in vacuum-electron beam systems, due to repulsive Coulomb force between the electrons, the electron beam may be scattered to cause a decrease of beam current. In the present electron beam system, the decrease of the beam current can be suppressed by the existence of ions in the anode plasma.

EXAMPLE 1

Figure 7:
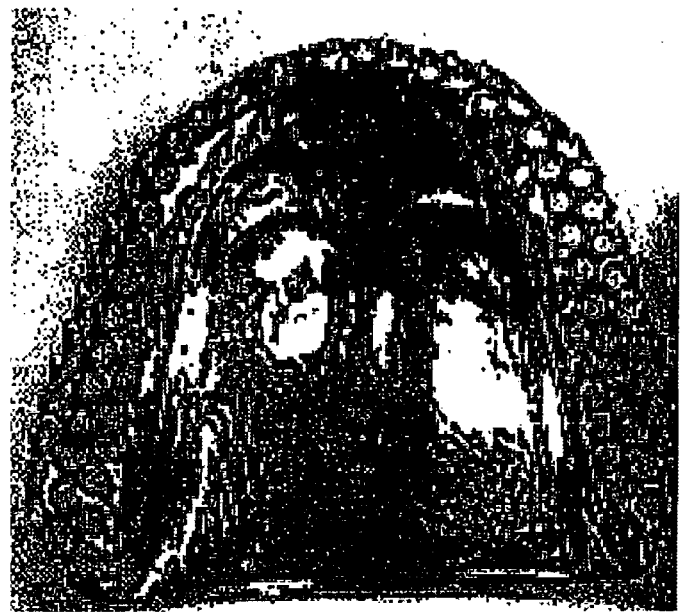
FIG. 7 shows metal and/or partial metal dentures in accordance with the invention.

The metal and/or partial metal dentures 12 are set on the rotating sample holder 13. The beam energy density was 3 J/cm$^2$. After the electron beam bombardment with 5 pulses repetition, the as-cast metal and/or partial metal dentures show metallic glittering surface and amorphous layer (the dentures being shown in FIG. 7). This indicates that the hand polishing with diamond tools are not required. When the rotating metal holder is thermally insulated with rock wool, the surface melts down further than expected.

EXAMPLE 2

Reducing the accelerated voltage from 30, 27, 25 kV and the remained partial gas pressure was increased as the irradiated energy is reduced. When the irradiated energy is lower than 0.1 J/cm$^2$ on the metal and/or partial metal dentures, any surface reaction was not observed even in the case of low melting alloys as Magnesium, Titanium, and high thermal conductive metal as Aluminum.

EXAMPLE 3

When the pulse repetition exceeds 100 with an energy density of 3 J/cm$^2$, the metal and/or partial metal dentures are deformed and they lose their ability to fit into the wearer's mouth. On the other hand, no surface modification was observed with pulse repetition over 30 with an energy density of 0.1 j/cm$^2$.

EXAMPLE 4

Figure 4:
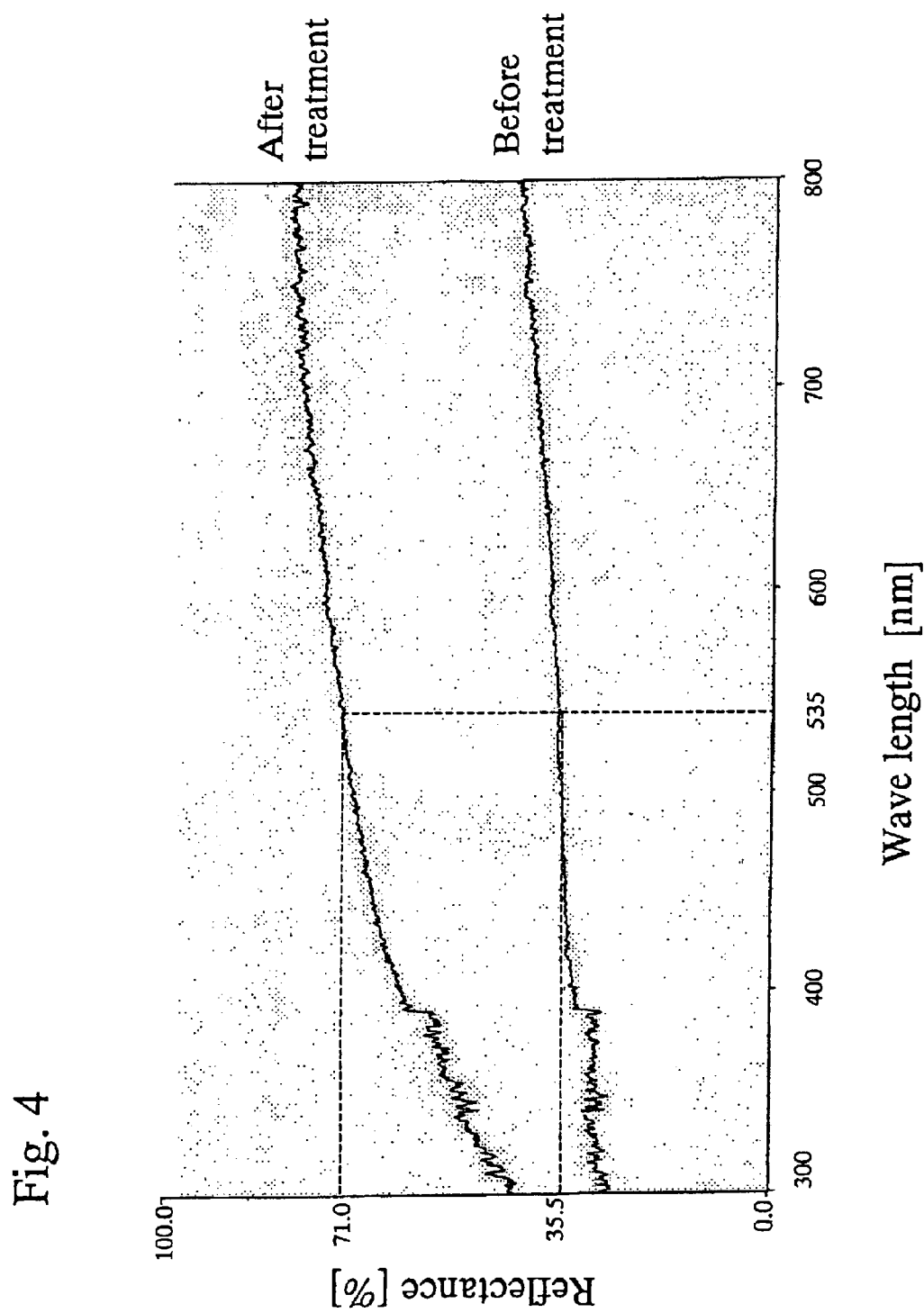
FIG. 4 shows the visible light reflection ratio from the metal and/or partial metal dentures before and after treatment in accordance with the invention.

After the electron beam irradiation with condition stated in Example 1 (i.e., energy density is 3 J/cm$^2$, pulse duration is 1.5 μs and pulse repetition is 5 times), the surface of the metal and/or partial metal dentures shows the equivalent reflectance as dentures polished by the dental specialist with diamond hand tools. To indicate the reflection ratio numerically, we applied spectroscopy analysis against reflected beam with the beam length range of 300 to 800 nm with the results being shown in FIG. 4.

To make the increase in the reflection ratio clear, the silver metal was applied against the light beam wavelength from 300 nm to 800 nm. In comparison to an untreated sample, the light beam reflection ratio was remarkably increased after the pulsed electron beam bombardment.

At almost maximum peak wavelength (i.e., 535 nm), the reflection rate after electron beam irradiation was 71% from the metal and/or partial metal dentures. On the other hand, the metal and/or partial metal dentures before the electron beam irradiation was 35.5%. In this case, the materials of the substrate used for the metal and/or partial metal dentures are an Ag—Pd—Au system alloy.

EXAMPLE 5

Figure 5:
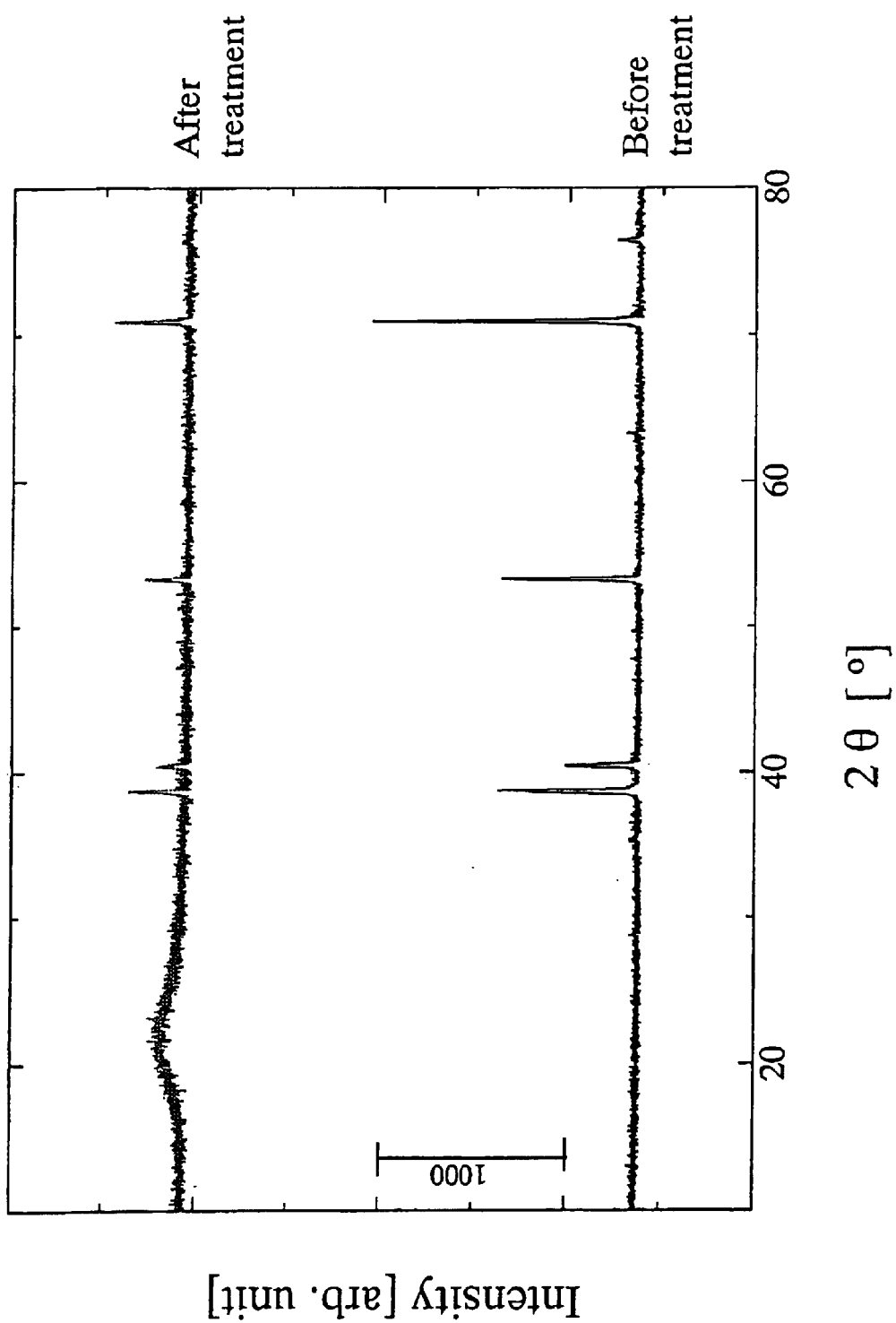
FIG. 5 shows the X-ray diffraction for samples before and after the pulsed electron irradiation.

To the metal and/or partial metal dentures made with Titanium system alloys, X-ray diffraction is applied to determine the surface crystal phase. The result is shown in FIG. 5 for the before and after electron beam irradiation on the metal and/or partial metal dentures. For the before electron beam irradiation metal dentures, titanium peaks are observed, on the other hand, titanium peaks could not be found in the dentures of the after electron beams irradiation except some peaks from re-crystallization. This shows that the surface of metal and/or partial metal dentures after the electron beam irradiation turned into amorphous.

EXAMPLE 6

Figure 6:
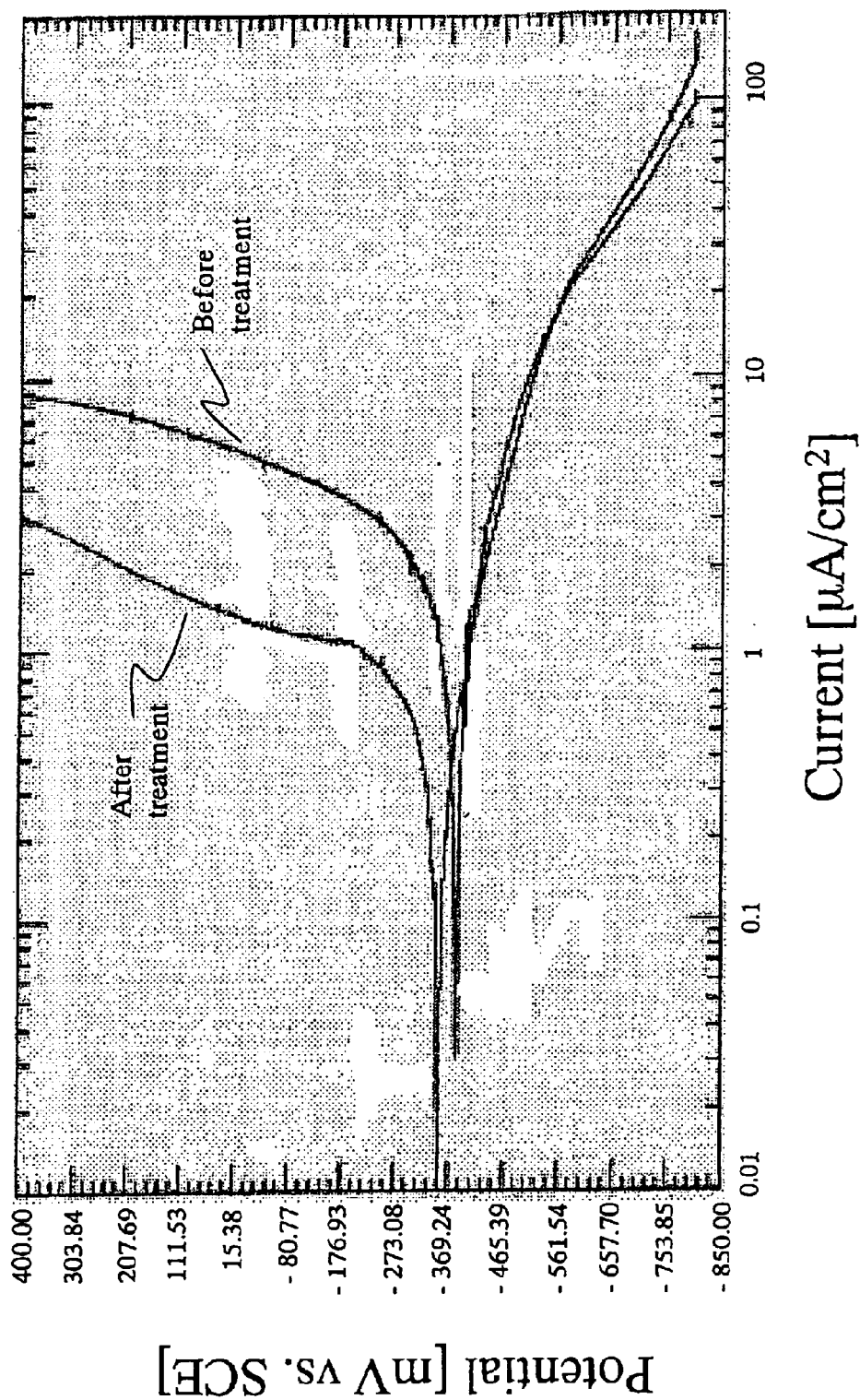
FIG. 6 shows the results of anodic polarization of before and after pulsed electron beam irradiation onto pure Titanium metal dentures, in which, the counter electrode material is platinum and the solution was 1 Normal Hydrochloride water solution.

To determine how the corrosion resistance was modified through the electron beam irradiation, Anodic polarity method was applied on pure Titanium as the result is shown in FIG. 6. Applying the Tafel equation, the corrosion electric current was compared between the after electron beam irradiated and the before electron beam irradiated. This was measured in 1N HCl water solution.

As the result, the corrosion electric current show 0.03 μA/cm$^2$ and 0.01 μA/cm$^2$, respectively. This means that the metal and/or partial metal dentures after electron beam irradiation have three times stronger resistance than the non-irradiated metal and/or partial metal dentures.

EXAMPLE 7

The amplitude of the applied voltage to the accelerating gap exceeds than 50 kV. After the pulse repetition exceeds 3, the metal and/or partial metal dentures were thermally deformed though it indicated mirror and amorphous surface.

EXAMPLE 8

The electron beam irradiation was done in a continued mode. For the heat cycle diffusion, heating and rapid cooling cannot be done well and a homogeneous amorphous surface could not be obtained.

EXAMPLE 9

Pulse duration was varied and when the duration was shorter than 0.5 μs, microcracks were observed on the surface of metal and/or partial metal dentures, so the corrosion resistance decreases essentially. When the duration is over 10 μs, the non-homogeneous surface could be obtained. This relation is summarized as $$\tau \approx k \cdot r^2 / a \qquad (1)$$

where r is an extrapolated penetration depth of the electrons in material, $a = \lambda / p \cdot c$ is thermal diffusivity, λ, p, c are thermal conductivity, density, and heat capacity, respectively.

For most materials, the value of a belongs in the range from 0.06 (for Ti) to 1.12 $cm^2/s$ (for Cu). Concerning the value of r, it belongs in the range (at electrons energy 20–40 keV) from 0.5–1.3 μm (for W) to 3.3–9.3 μm (for Al), correspondingly.

The coefficient k depends on the material properties, namely it is defined by the relation between a and r. To provide a high efficiency of the surface heating, on one hand, and to decrease the thermal stresses defined by the temperature gradients in a surface layer on the other hand, the value of k is chosen by the following way:

a) for most constructive metallic alloys (alloys on the base of Fe, Al, and Ti), the coefficient k≈1÷5.

b) for materials having high temperature conductivity and a small value of penetration depth r (Cu, Mo<W and alloys based on them), the coefficient k should be equal k≈10÷50.

Using Eq. 1 and taking into account the limitations of k, one can obtain the range of the beam pulse duration τ≈0.5÷10 μs.

What is claimed is:

1. A method for forming dentures, comprising the steps of:
    generating electron beams; and
    directing the electron beams to an at least partially metal substrate having the form of teeth to provide the substrate with at least one polished, amorphous surface.

2. The method of claim 1, wherein the step of generating the electron beams comprises the step of generating electron beams in pulsed repetition.

3. The method of claim 2, wherein the pulse repetition is less than 100.

4. The method of claim 2, wherein the duration of the pulses is from 0.5 μs to 10 μs.

5. The method of claim 2, wherein the pulse repetition is less than 100, the duration of the pulses is from 0.5 μs is to 10 μs and the irradiated energy is greater than 0.1 $J/cm^2$.

6. The method of claim 1, wherein the irradiated energy is greater than 0.1 $J/cm^2$.

7. The method of claim 1, wherein the electron beam is directed onto an entire surface of the denture base.

8. The method of claim 1, further comprising the steps of:
    placing the substrate in a vacuum chamber; and
    evacuating the chamber and then directing inert gas into the chamber.

9. The method of claim 1, further comprising the step of adjusting the pressure of the inert gas in the chamber to a pressure between $0.5 \times 10^{-1}$ Pa and $3 \times 10^{-1}$ Pa.

10. The method of claim 9, wherein the pressure of the inert gas is adjusted by a flow control valve associated with the chamber.

11. The method of claim 1, wherein the substrate is entirely metal.

12. The method of claim 1, wherein the substrate is only partially metal.

13. The method of claim 1, further comprising the step of placing the substrate on a beam collector in a position to receive the electron beams.

14. The method of claim 1, further comprising the step of placing the substrate on a rotating sample holder in a position to receive the electron beams.

15. The method of claim 1, wherein the electron beams are generated and directed to the substrate such that only a surface of the substrate is polished and rendered amorphous.

16. The method of claim 1, wherein the substrate is made of an Ag—Pd—Au alloy.

17. The method of claim 1, wherein the substrate is made of titanium system alloys.

18. The method of claim 1, wherein the electron beams are generated and directed to the substrate such that the at least one polished, amorphous surface exhibits corrosion resistance.

* * * * *